(12) United States Patent
Ginn

(10) Patent No.: US 6,776,784 B2
(45) Date of Patent: Aug. 17, 2004

(54) CLIP APPARATUS FOR CLOSING SEPTAL DEFECTS AND METHODS OF USE

(75) Inventor: Richard S. Ginn, San Jose, CA (US)

(73) Assignee: Core Medical, Inc., Sunnyvale, CA (US)

( * ) Notice: Subject to any disclaimer, the term of this patent is extended or adjusted under 35 U.S.C. 154(b) by 0 days.

(21) Appl. No.: 09/948,502

(22) Filed: Sep. 6, 2001

(65) Prior Publication Data

US 2003/0045893 A1 Mar. 6, 2003

(51) Int. Cl.$^7$ .................. A61B 17/08; A61B 17/10; A61D 1/00
(52) U.S. Cl. .............. 606/151; 606/142; 606/219; 606/221
(58) Field of Search .................. 606/151, 153, 606/157, 213, 219

(56) References Cited

U.S. PATENT DOCUMENTS

| | | | | |
|---|---|---|---|---|
| 4,741,336 A | * | 5/1988 | Failla et al. ............. 227/181.1 |
| 4,802,478 A | * | 2/1989 | Powell ........................ 606/138 |
| 4,878,893 A | * | 11/1989 | Chin ............................ 604/21 |
| 5,108,420 A | | 4/1992 | Marks ........................ 606/213 |
| 5,334,217 A | | 8/1994 | Das ............................ 606/213 |
| 5,554,162 A | * | 9/1996 | DeLange ................... 606/153 |
| 5,702,421 A | | 12/1997 | Schneidt .................... 606/213 |
| 5,713,911 A | * | 2/1998 | Racenet et al. ............. 606/157 |
| 5,725,554 A | * | 3/1998 | Simon et al. ................ 606/219 |
| 5,879,366 A | | 3/1999 | Shaw et al. ................. 606/213 |
| 5,919,200 A | | 7/1999 | Stambaugh et al. ........ 606/159 |
| 5,944,738 A | | 8/1999 | Amplatz et al. ............ 606/213 |
| 6,007,563 A | | 12/1999 | Nash et al. ................. 606/213 |
| 6,036,720 A | | 3/2000 | Abrams et al. ............. 606/213 |
| 6,077,281 A | | 6/2000 | Das ............................ 606/151 |
| 6,077,291 A | | 6/2000 | Das ............................ 606/213 |
| 6,080,182 A | | 6/2000 | Shaw et al. ................. 606/213 |
| 6,206,907 B1 | | 3/2001 | Marino et al. .............. 606/215 |
| 6,270,515 B1 | | 8/2001 | Linden et al. .............. 606/213 |
| 6,346,112 B2 | * | 2/2002 | Adams ....................... 606/157 |
| 2003/0033006 A1 | * | 2/2003 | Phillips et al. ............. 623/1.36 |

* cited by examiner

Primary Examiner—Michael J. Milano
Assistant Examiner—P. Roberts
(74) Attorney, Agent, or Firm—Orrick, Herrington & Sutcliffe LLP; James W. Geriak

(57) ABSTRACT

A device for closing a septal defect, such as a patent foramen ovale, includes a clip formed from a superelastic material that is inserted into a septum wall of a heart. The clip is advanced through a patient's vasculature, e.g., within a delivery apparatus, until the clip is disposed within a first chamber adjacent the septal defect. Tines of the clip are directed through a flap of tissue of the septal defect until the tines of the clip are disposed within a second opposing chamber. The clip then transforms into its relaxed state, wherein the tines of the clip engage with a surface of the second chamber, thereby substantially closing the septal opening.

8 Claims, 5 Drawing Sheets

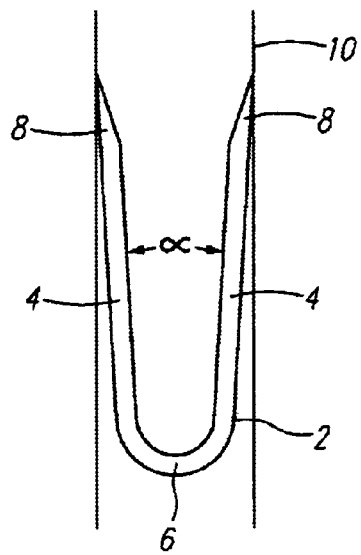
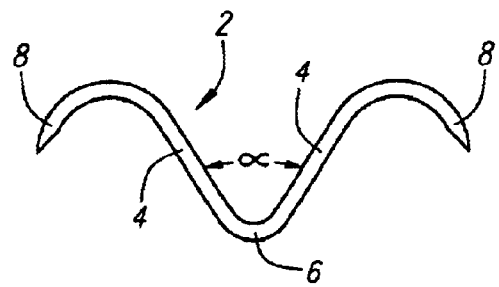
FIG. 1
FIG. 2
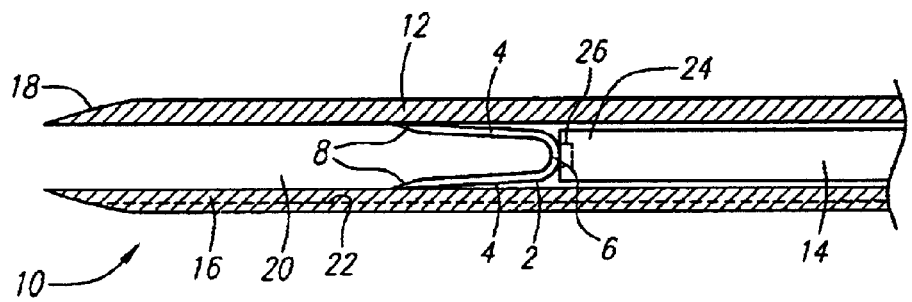
FIG. 3
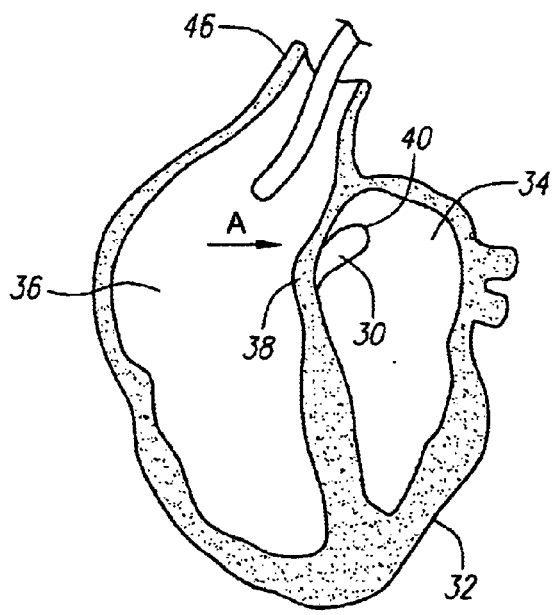
FIG. 4

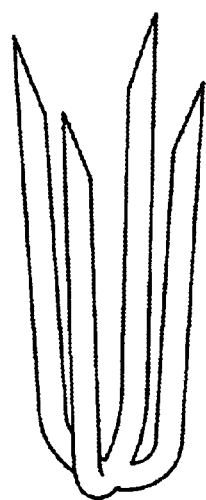
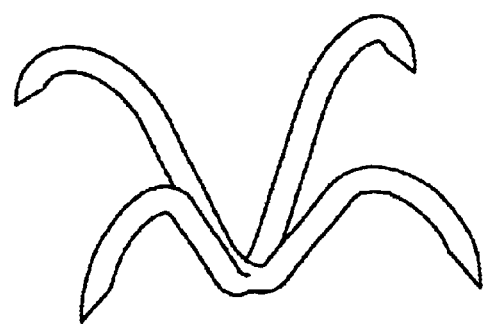
*FIG. 8*
*FIG. 9*
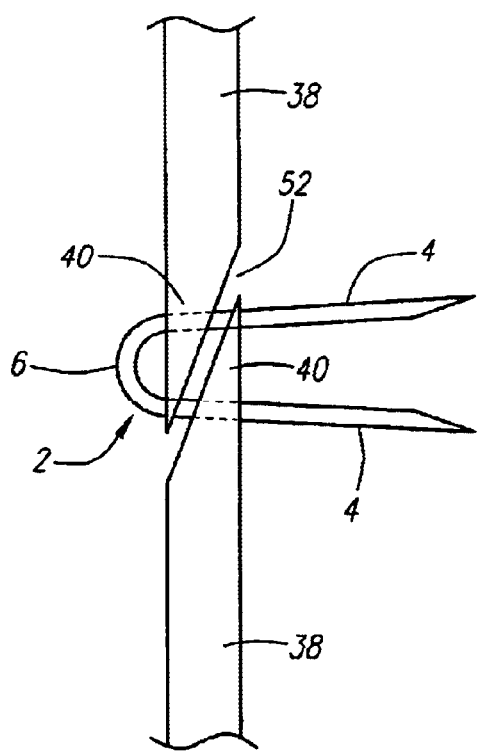
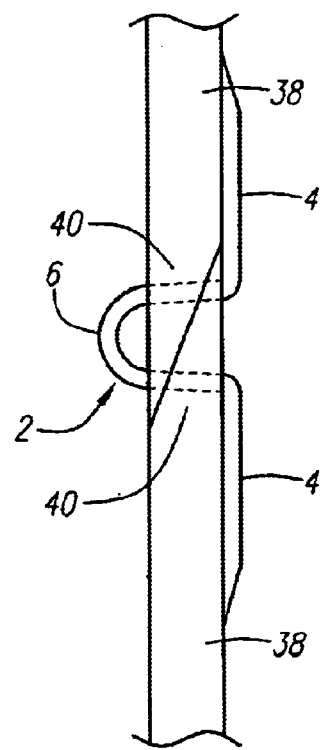
*FIG. 10*
*FIG. 11*

CLIP APPARATUS FOR CLOSING SEPTAL DEFECTS AND METHODS OF USE

FIELD OF THE INVENTION

The present invention relates generally to apparatus and methods for treating septal defects, and more particularly to apparatus and methods for closing a patent foramen ovale or other septal defect.

BACKGROUND

During development of a fetus in utero, blood is generally oxygenated by the mother's placenta, not the fetus' developing lungs. Most of the fetus' circulation is shunted away from the lungs through specialized vessels or foramens that are open during fetal life, but generally close shortly after birth. Occasionally, however, these foramen fail to close and create hemodynamic problems, which may ultimately prove fatal unless treated.

One defect that may occur is a patent foramen ovale ("PFO"), which may occur between the left and right atria of the heart. During fetal life, an opening called the foramen ovale allows blood to pass directly from the right atrium to the left atrium (bypassing the lungs). Thus, oxygenated blood from the placenta may travel through the vena cava into the right atrium, through the foramen ovale into the left atrium, and from there into the left ventricle for delivery via the aorta to the fetus' body. After birth, with pulmonary circulation established, the increased left atrial blood flow and pressure causes the functional closure of the foramen ovale. This closure is then followed by the anatomical closure of the foramen ovale.

In some humans, however, the foramen ovale fails to completely close. This condition can pose serious health risks for the individual, particularly if the individual has other heart abnormalities. For example, recent studies suggest an association between the presence of a patent foramen ovale and the risk of paradoxical embolism or stroke. See P. Lechat J et al., *Prevalence of Patent Foramen ovate in Patients with Stroke*, N. Engl. J. Med. 1988;318: 1148–1152.

Still other septal defects may occur within a septum between the various chambers of the heart, such as atrial-septal defects (ASDs), ventricular-septal defects (VSDs), and the like. To close such defects, open heart surgery may be performed to ligate and close the defect. Such procedures are obviously highly invasive and pose substantial morbidity and mortality risks.

Alternatively, catheter-based procedures have been suggested. These may involve introducing umbrella or disk-like structures into the heart that include opposing expandable structures connected by a hub or waist. Generally, the device is inserted through the defect, and the expandable structures are deployed on either side of the septum to secure the tissue surrounding the defect between the umbrella or disk-like structure in an attempt to seal and close the defect. Such devices, however, involve frame structures that often support membranes, either of which may fail during the life of the patient being treated, opening the defect and/or releasing segments of the structure within the patient's heart.

Accordingly, apparatus and methods for closing septal defects, and in particular a patent foramen ovale, would be considered useful.

SUMMARY OF THE INVENTION

The present invention is directed to apparatus and methods for closing septal defects, including, but not limited to, a patent foramen ovale.

In a first aspect of the invention, an apparatus for closing a septal defect includes a clip formed from a elastic material having at least two penetrating tines and an opposing retaining end. The clip is biased so as to project the at least two penetrating tines distal to the opposing retaining end, wherein when the bias is removed, the at least two penetrating tines move laterally apart from one another.

In accordance with another aspect of the present invention, a delivery apparatus for delivering a clip, such as that described above, is provided that includes an outer catheter and a pusher member that are slidably coupled to one another. The catheter may be a tubular member including proximal and distal ends and a lumen therebetween, the distal end having a size for insertion into a blood vessel or other body lumen. The clip may be carried within the lumen of the outer catheter, preferably, with the tines disposed distally to the retaining end.

The pusher member may be an inner catheter or other elongate member that is disposed within the lumen of the outer catheter. The pusher member may include a distal end that may be disposed proximate the retaining end of the clip, the pusher member being movable axially relative to the tubular member for ejecting the clip distally from the lumen.

An actuator may be provided on the proximal end of the tubular member and/or the pusher member for advancing the pusher member relative to the tubular member. Preferably, the actuator may limit advancement of the pusher member.

In a further alternative, the delivery apparatus may include an imaging device including an imaging element associated with the distal end of the tubular member for imaging near or beyond the distal end of the tubular member. For example, the imaging device may be an angioscope or ultrasound device that may be received within a lumen of the tubular member or may be a separate device that may introduced independently into the patient but used in conjunction with the delivery apparatus during a procedure.

In another alternative, the clip has a single tine and an opposing retaining end. The clip is biased so as to project the single tine distal to the opposing retaining end. When the bias is removed, the clip transforms into a geometric shape such as a "V", "U", "S", or "L". The opposing retaining end may have an optional head to prevent the clip from completely passing through the septum wall of a heart.

In accordance with yet another aspect of the present invention, a method is provided for closing a patent foramen ovale or other septal defect within a patient's heart. Generally, the septal defect includes one or more flaps of tissue partially detached from a septum wall between first and second chambers of the heart, the flap(s) of tissue and surrounding tissue of the septum wall defining a septal opening through the septum wall.

A clip, such as that described above, is advanced, in a stressed state, through the patient's vasculature until the clip is disposed adjacent to the septal opening. The tines of the clip penetrate the flap of tissue and pass into the second chamber of the heart. After the clip has penetrated the flap of tissue (i.e., septal defect), the clip transitions to its relaxed state so as to at least partially close the septal opening.

It is an object of the invention to provide a clip apparatus for the closure of septal defects, such as a patent foramen ovale. It is a further object of the invention to provide a delivery device for the delivery of the clip apparatus to the defect area. It is yet a further object of the invention to provide a method of closing a patent foramen ovale using the clip apparatus. Other objects and features of the present invention will become apparent from consideration of the following description taken in conjunction with the accompanying drawings.

BRIEF DESCRIPTION OF THE DRAWINGS

FIG. 1 is a cross-sectional view of a clip apparatus showing the clip in a stressed state.

FIG. 2 is a cross-sectional view of the clip shown in FIG. 1 with the clip in a relaxed state.

FIG. 3 is a cross-sectional view of a delivery apparatus showing a pusher member and a clip contained within a lumen of the delivery apparatus.

FIG. 4 is a cross-sectional view of a heart including a septal foramen ovale in a septum wall of the heart. The delivery apparatus of FIG. 3 is shown being advanced through the aortic arch.

FIG. 8 is a perspective view of a clip according to a separate preferred aspect of the invention. The clip is shown in its stressed state.

FIG. 9 is a perspective view of the clip shown in FIG. 8 with the clip in its relaxed state.

FIG. 10 is a cross-sectional view of the septum wall showing a hole-type septal defect. The clip is shown in its stressed state.

FIG. 11 is a cross-sectional view of the septum wall showing a hole-type septal defect. The clip is shown in its relaxed state.

DETAILED DESCRIPTION OF THE PREFERRED EMBODIMENTS

Figure 5:
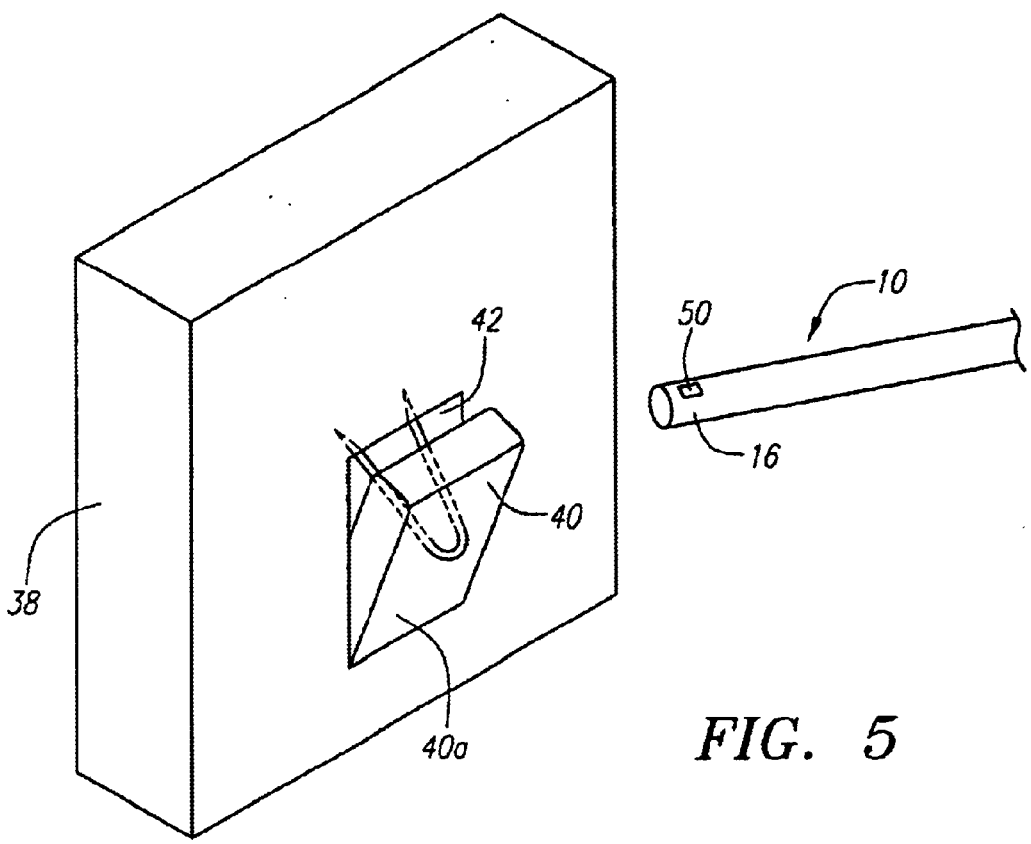
FIG. 5 is a perspective detail view of the septal defect shown in FIG. 4. A flap of tissue, which is partially attached to the septum, has been pierced by the clip in its stressed state.

FIGS. 1 and 2 illustrate a first preferred embodiment of a clip 2 that is used for closing a septal defect (i.e., PFO, ASA, VSA), in accordance with the present invention. The clip 2 includes two penetrating tines 4 that are connected to one another via an opposing retaining end 6. The tips 8 of the tines 4 are sharpened to aid in penetrating tissue. In FIG. 1, the clip 2 is shown in its stressed state. In this regard, the clip 2 may by made from an elastic material, such as stainless steel, and preferably, a superelastic material. Alternatively, the clip 2 may be formed from a shape memory alloy, one example being NITINOL. Of course, other bio-compatible elastic or superelastic materials may also be employed. The clip 2 is maintained in its stressed state by restraining the tines 4 from expanding outward. In this manner a biasing force is applied to the clip 2. The tines 4 of the clip 2 project distally from the retaining end 6, as is shown, for example, in FIG. 1. The tines 4 preferably are restrained by using a delivery apparatus 10, such as a catheter or the like (discussed in more detail below). Preferably, in its stressed state, the clip 2 has the shape of a "U" or a "V", as is shown, for example, in FIG. 1.

FIG. 2 illustrates the clip 2 in its relaxed state. Without the application of the biasing force, the clip 2 transitions to its related configuration wherein the angle α between the two tines 4 increases. The tines 4 also move laterally away from one another, as is shown, for example, in FIG. 2. In addition, portions of the tines 4 closest to the tips 8 may optionally inflect back upon themselves. In one preferred embodiment, in the final relaxed configuration, the clip 2 preferably has the shape of a "W", as is shown, for example, in FIG. 2.

Depending on the type and nature of the septal defect, the clip 2 may have variations in its design. For example, the length of the tines 4 may be chosen depending on the size of the opening 42. If the opening is larger, longer tines 4 may be used. Similarly, a larger opening 42 may require a greater expansion angle α for the clip. Other variations may also be present, such as the degree of inflection, if any, in the ends of the tines 4 nearest the tips 8. The clip 2 may be made of one piece of material or, alternatively, multiple segments.

Referring now to FIG. 3, a delivery apparatus 10 generally includes an outer catheter or tubular member 12, and an inner catheter or pusher member 14. The outer catheter 12 includes a proximal end (not shown), and a distal end 16 having a size suitable for insertion into a blood vessel or other body lumen (not shown). The distal end 16 preferably has a tapered or rounded tip 18, e.g., for facilitating substantial atraumatic advancement of the delivery apparatus 10 through the patient's vasculature. The outer catheter 12 also includes a lumen 20 therein that extends between proximal and distal ends 16. As shown in FIG. 3, the clip 2 is contained within the lumen 20 of the outer catheter 12. The outer catheter 12 provides the biasing force to keep the clip 2 in its stressed state.

In one preferred embodiment of the invention, the outer tubular member 12 may include one or more axially disposed grooves 22 (one is shown in FIG. 3) within the inner surface that engages with the tine(s) 4 of the clip 2. The groove(s) 22 may serve as a guide for the clip 2 so that the orientation of the clip 2 is maintained during delivery. In this regard, the clip 2 may not rotate into a different orientation as it is ejected from the outer catheter 12.

The pusher member 14 includes a proximal end (not shown) and a distal end 24 having a size such that the pusher member 14 may be slidably disposed within the lumen 20 of the outer catheter 12. The distal end 24 may be disposed proximal to the retaining end 6 of the clip 2, and the pusher member 14 may be moveable axially relative to the outer catheter 12 for ejecting the clip 2 distally from the lumen 20, as is described more fully below. Optionally, the distal end 24 of the pusher member 14 may contain a notch 26 that engages with the retaining end 6 of the clip 2 for assisting in orienting of the clip 2. The notch 26 may prevent the rotation of the clip 2, or alternatively, aid in rotating the clip 2 (through rotation of the pusher member 14) for proper orientation. The notch 26 may be present without or in addition to the groove(s) 22.

An actuator, e.g., a handle device (not shown), may be provided on the proximal end of the outer catheter 12 and/or the pusher member 14.

Figure 6:
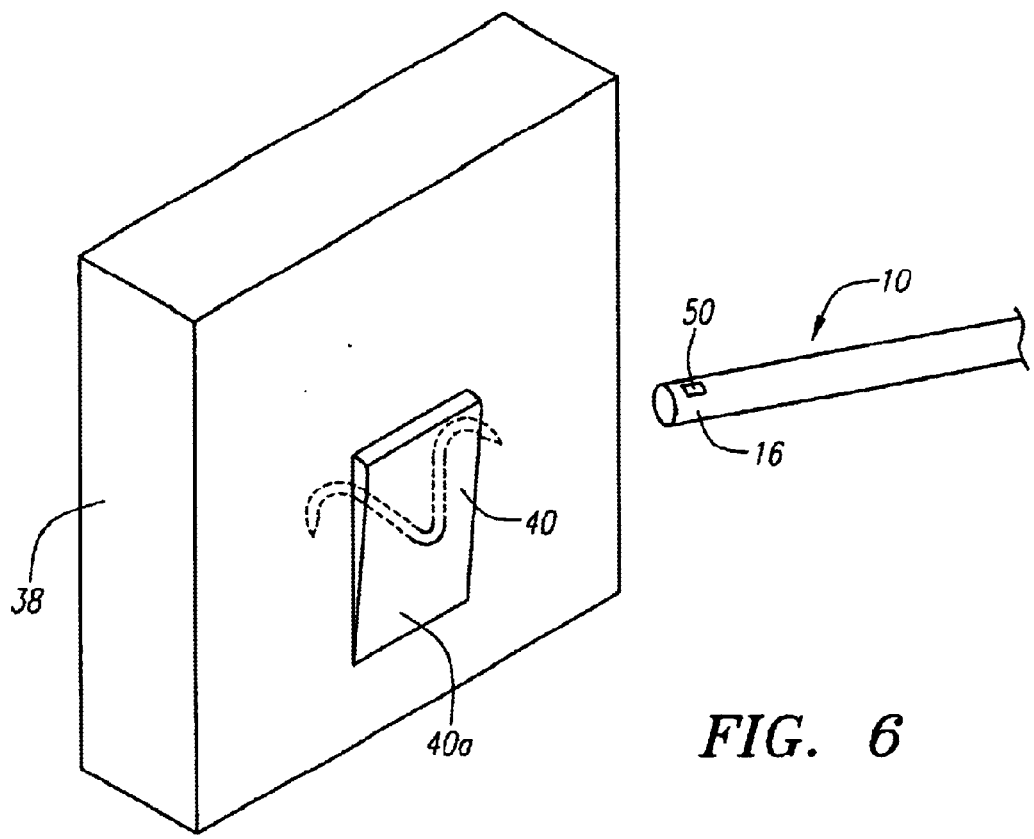
FIG. 6 is a perspective detail view of the septal defect shown in FIG. 4 after deployment of the clip apparatus. The flap of tissue has closed the opening after the clip has transitioned to its relaxed state.

Use of the clip 2 for closing a septal defect 30 is shown in conjunction with FIGS. 4–7(c), 10, and 11. FIG. 4 generally shows a heart 32 of a patient, including heart chambers 34, 36 separated by a septum wall 38. The septal defect 30, which may be a PFO, ASD, VSD and the like, is shown in the septum wall 38. As best seen in FIGS. 5 and 6, the septal defect 30 may include a flap of tissue 40 adjacent to an opening 42 in the septum wall 38. FIGS. 10 and 11 illustrate another septal defect 30 wherein the defect is a hole-type of structure 52, e.g., extending laterally through the septum wall 38.

The delivery apparatus 10, with the clip 2 therein, may be introduced into the patient's vasculature, e.g., from a percutaneous entry site in a peripheral vessel, such as the femoral vein, jugular vein, and the like (not shown). The distal end of the outer catheter 12, including the clip 2, may be advanced endoluminally within the patient's vasculature, e.g., through the vena cava 46 (inferior or superior) and into the heart 32 until the distal end 16 is disposed within the chamber 34, which is shown in FIG. 4 to be the right atrium. Alternatively, the clip 2 may be introduced using an arterial approach as is commonly known in the art.

Figure 7A:
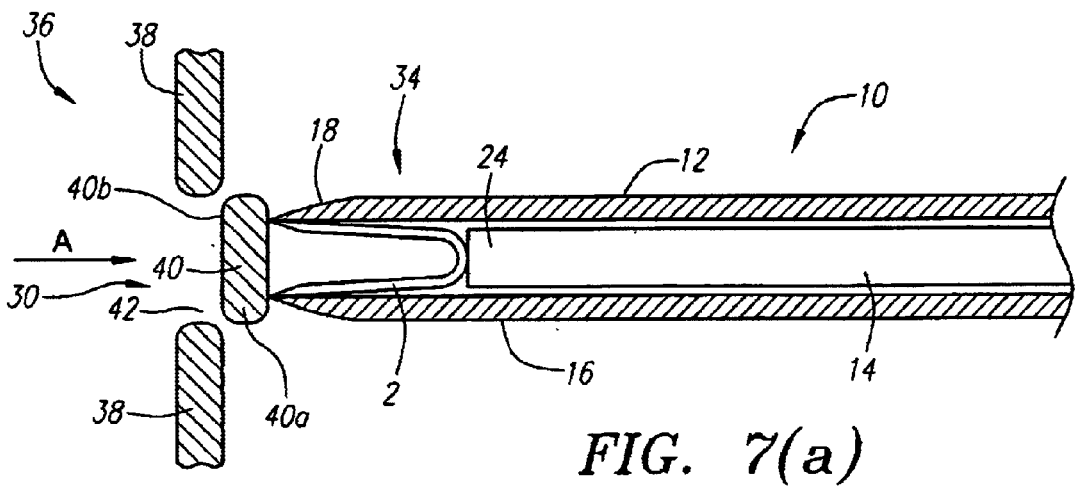
FIG. 7(a) is a cross-sectional view of the septum wall and delivery device, showing a method for closing the septal defect shown in FIGS. 4–6. The delivery device is shown adjacent to the flap of tissue.

With particular reference to FIGS. 5, 6, and 7(a)–(c), the distal end 16 of the delivery apparatus 10 may be advanced into contact with a proximal surface 40a of the flap of tissue 40, e.g., such that the flap of tissue 40 is disposed proximate the septal opening 42, as shown in FIG. 7(a). The pusher member 14 may be advanced distally relative to the outer catheter 12, thereby piercing the tines 4 of the clip 2 through the flap of tissue 40 until a portion of the tines 4 of the clip 2 are located within the second chamber 36 located on the opposing side of the septum wall 38, thereby creating punctures 48 for each tine 4. The penetrating tips 8 on the tines 4 of the clip are preferably sharp enough to facilitate piercing and passing of the tines 4 through the flap of tissue 40.

Preferably, the pusher member 14 is advanced distally to aid in pushing the tines 4 of the clip 2 through the flap of tissue 40. The pusher member 14 preferably pushes until the clip 2 cannot advance further through the flap of tissue 40 (i.e., the retaining end 6 of the clip 2 prevents further advancement). This may be accomplished by using an actuator (not shown) on the delivery apparatus 10 that permits controlled advancement of the pusher member 14. For example, the actuator may allow the distal end 24 of the pusher member 14 to be disposed at a location within or external to the distal tip 18 of the outer catheter 12.

Figure 7B:
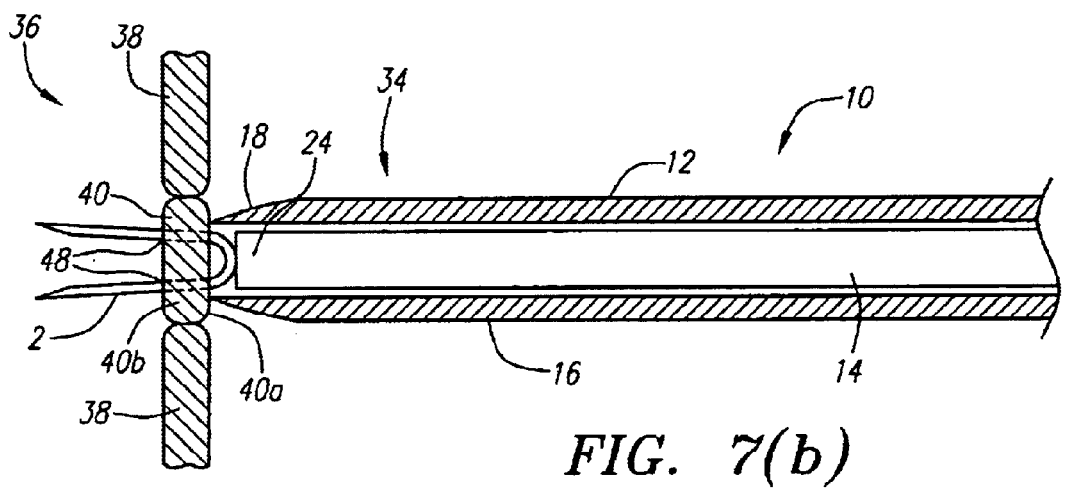
FIG. 7(b) is a cross-sectional view of the septum wall and delivery device, showing a method for closing the septal defect shown in FIGS. 4–6. The pusher member has deployed the clip through the flap of tissue.
Figure 7C:
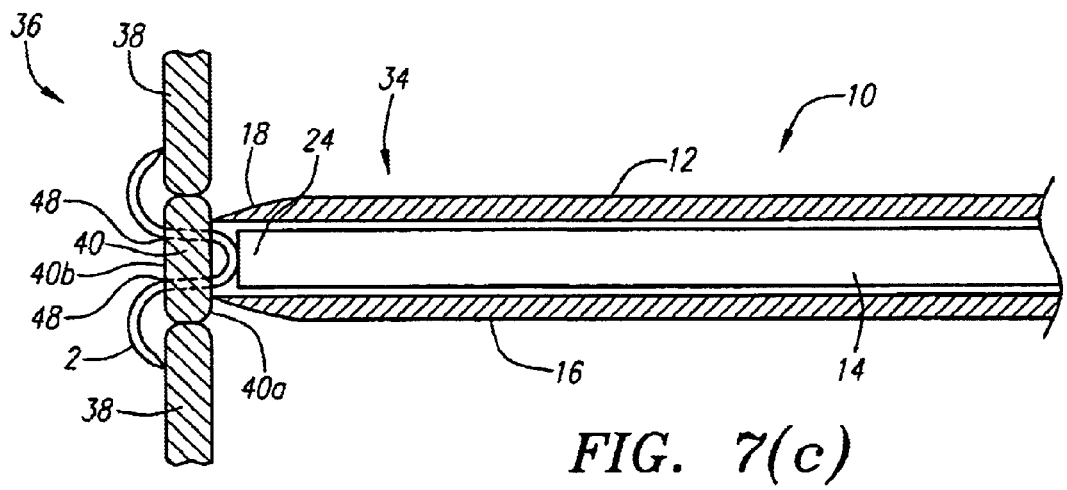
FIG. 7(c) is a cross-sectional view of the septum wall and delivery device, showing a method for closing the septal defect shown in FIGS. 4–6. The clip has transitioned to its relaxed state and closed the septal defect.

FIG. 7(b) shows the clip 2, still in its stressed state, puncturing the flap of tissue 40. The nature of the material of the clip 2 is such that the clip 2 remains in the stressed state as the tines 4 pierce the flap of tissue 40. After the clip 2 has passed through the flap of tissue 40, the clip 2 begins its transformation from the stressed state to the relaxed state shown, for example, in FIG. 2. FIG. 7(c) shows the clip 2 after it has passed into the relaxed state. In this embodiment, the tips 8 of the tines 4 have inflected back in the direction of the retaining end 6 of the clip 2. In doing so, the tips 8 of the clip 2 preferably engage with the septum wall 38 on opposing sides of the flap of tissue 40. While it is preferable that both tips 8 be engaged with the septum wall 38 to properly close the opening 42, it may still be possible to close the opening 42 if only one of the tips 8 engages with the septum wall 38.

As best seen in FIG. 6, in which a perspective detail view of the region of the septum wall 38 having the septal defect 30 is shown, the opening 42 between the first and second chambers 34, 36 has been eliminated by the placement of the clip 2 in the flap of tissue 40. By engaging with the septum wall 38, the tips 8 of the clip 2 may prevent the flap of tissue 40 from moving proximate to the septum wall 38 in the first chamber 34 (as is shown in FIG. 7(a)).

FIGS. 8 and 9 show an alternative preferred embodiment of the clip 2 wherein the clip 2 has four tines 4 as opposed to the two tines 4 shown in FIGS. 1–7(c), 10, and 11. FIG. 8 shows the clip 2 in a stressed state while FIG. 9 shows the clip 2 in a relaxed state. The additional tines 4 may increase the chances that one or more tines 4 will properly be secured to the septum wall 38 upon deployment. While clips 2 having two and four tines 4 have been specifically disclosed herein, it should be understood that the clip 2 may have any number of tines 4 in excess of one, including even and odd numbers of tines 4.

It will be appreciated by those skilled in the art that the procedure described herein may be monitored in a variety of ways. For example, the delivery apparatus 10 may include an imaging device 50 (FIGS. 5 and 6), such as an angioscope or other fiber optic device, intravascular ultrasound ("IVUS") device, and the like (not shown). The device may be provided on the distal end 16 of the outer catheter 12, e.g., attached to or adjacent the distal tip 18 or advanceable from a lumen (not shown) therein. In a further alternative, external imaging may be used, either alone or in conjunction with direct visualization. For example, the clip 2, the outer catheter 12, and/or the pusher member 14 may include radiopaque markers (not shown) at predetermined locations that may be observed using fluoroscopy and the like.

FIGS. 10 and 11 illustrate a preferred embodiment of the clip 2, wherein in its relaxed state (shown in FIG. 11), the tines 4 of the clip 2 lie substantially flat against the septum wall 38. This embodiment may be preferred for several reasons. First, a larger portion of the tines 4 may be in contact with the septum wall 38, giving the clip 2 a more secure hold to the flap(s) of tissue 40. Second, since at least a portion of the tines 4 lie substantially flat against the septum wall 38, less surface area of the clip 2 may be exposed to the patient's blood. Typically, a patient that receives a clip 2 may be administered anti-coagulant drugs to counteract the clotting of platelets on the surface of the clip 2. By reducing the amount of surface area of the clip 2 that is exposed to the blood, clotting problems may be reduced. FIG. 11 shows a cross-sectional view of the septum wall 38 with the clip 2 in its relaxed state. Preferably, the clip 2 is designed such that the tines 4 of the clip 2 lie substantially flat against the septum wall 38 on either side of the septal defect 30.

FIGS. 10 and 11 further illustrate the septum wall 38 containing a septal defect 30 in which the defect is a hole-type structure 52 that may pass laterally through the septum wall 38 of a heart 32. In this regard, the septal defect 30 is similar to two overlapping flaps of tissue 40. This type of septal defect 30 may be seen, for example, in patients having a PFO. The clip 2 may be delivered in a similar way to the method described above. Specifically, the clip 2 may puncture the two overlapping flaps of tissue 40 while the clip 2 is in its stressed state and, upon relaxation, at least a portion of the hole-type structure 52 may collapse, thereby preventing the flow of blood across the septum wall 38.

Figure 12A:
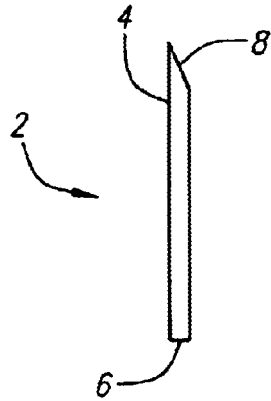
FIG. 12(a) is a cross-sectional view of a clip having a single tine in its relaxed state.
Figure 12B:
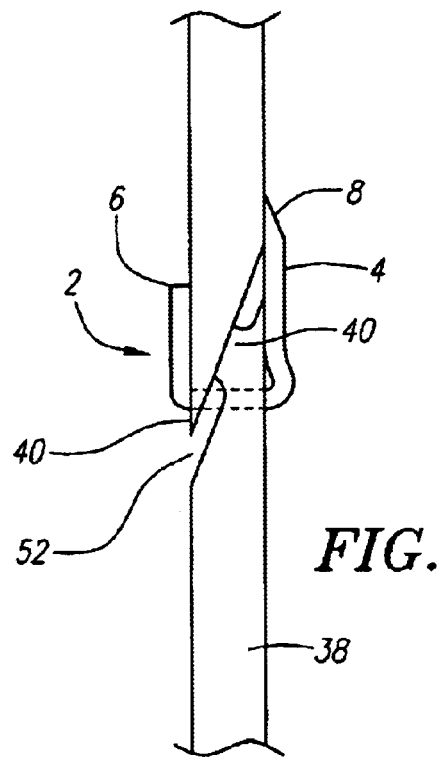
FIG. 12(b) is a cross-sectional view of the septum wall showing a hole-type septal defect.
Figure 13:
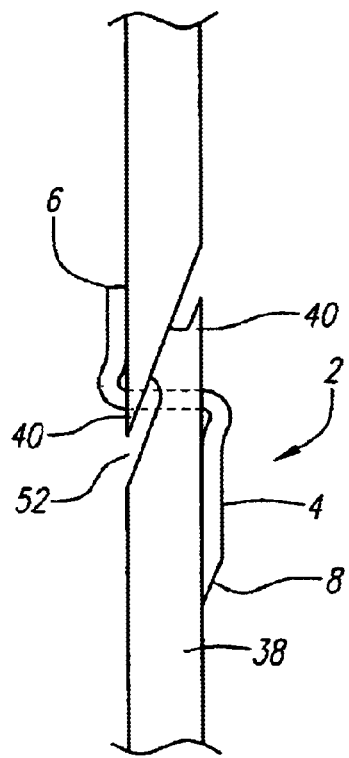
FIG. 13 is a cross-sectional view of the septum wall showing a hole-type septal defect. A clip having a single tine is shown in its relaxed state.
Figure 14A:
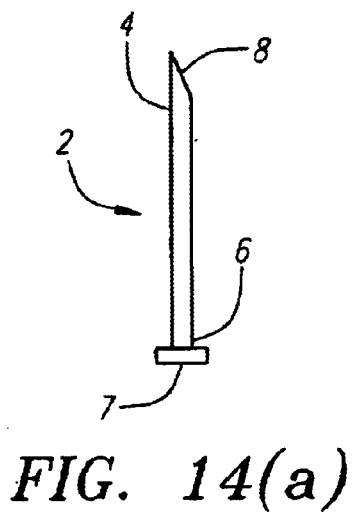
FIG. 14(a) is a cross-sectional view of a clip having a single tine in its relaxed state.
Figure 14B:
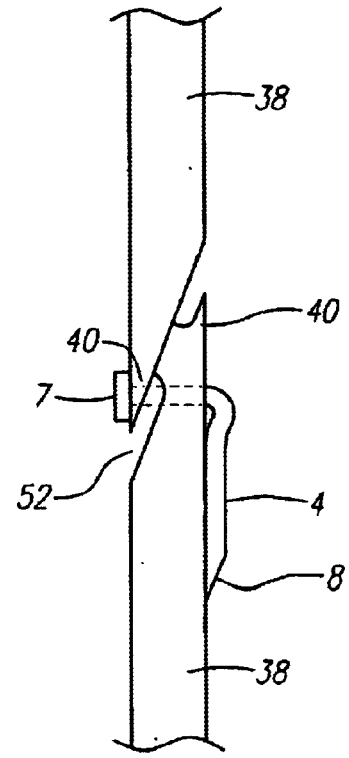
FIG. 14(b) is a cross-sectional view of the septum wall showing a hole-type septal defect.

In yet another embodiment of the invention, the clip 2 may have only a single tine 4. In its biased state, the clip 2 is substantially linear, as is shown, for example, in FIG. 12(*a*). The clip 2 is deployed by piercing one or more flap(s) of tissue 40 such that a portion of the clip 2 is one side of a septum wall 38 and the remaining portion is on the opposing side of the septum wall 38. Both "halves" of the clip 2 then bend from a stressed state to a relaxed state to close the septal defect. The clip 2 in its relaxed state may take the shape of a "U" or "V" (shown, for example, in FIG. 12(*b*)), or even an "S" (shown in FIG. 13). FIGS. 14(*a*)–(*b*) show yet another embodiment of a clip 2 having a single tine 4. In its biased state, the clip 2 is substantially linear, as is shown, for example, in FIG. 14(*a*). In this embodiment, the retaining end 6 of the clip 2 includes a head 7 that prevents the clip 2 from passing completely through the septum wall 38. In this regard, the clip 2, in its relaxed state, takes the shape of an "L" (shown, for example, in FIG. 14(*b*)). During deployment of this clip 2, the tine 4 is preferably advanced through the septum wall 38 until the head 7 prevents further advancement of the clip 2.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for closing a septal defect, comprising:
a clip formed from an elastic material having at least two penetrating tines and an opposing retaining end, the clip having a relaxed configuration in which the tines are inflected back on themselves, the clip being biased so as to project the at least two penetrating tines distal to the opposing retaining end, wherein when the bias is removed, the at least two penetrating tines move laterally apart from one another, a tubular member comprising proximal and distal ends and a lumen therebetween, the distal end having a size for insertion into a blood vessel, the clip being carried within the lumen such that the penetrating tines are disposed distally to the retaining end;
a pusher member slidably disposed within the lumen, the pusher member comprising a distal end disposed proximate to the retaining end of the clip, the pusher member being movable axially relative to the tubular member for ejecting the clip distally from the lumen; and
at least one axially disposed clip-retaining groove located in an inner surface of the tubular member.

2. An apparatus for closing a septal defect, comprising:
a clip formed from an elastic material having at least two penetrating tines and an opposing retaining end, the clip having a relaxed configuration in which the tines are inflected back on themselves, the clip being biased so as to project the at least two penetrating tines distal to the opposing retaining end, wherein when the bias is removed, the at least two penetrating tines move laterally apart from one another, a tubular member comprising proximal and distal ends and a lumen therebetween, the distal end having a size for insertion into a blood vessel, the clip being carried within the lumen such that the penetrating tines are disposed distally to the retaining end;
a pusher member slidably disposed within the lumen, the pusher member comprising a distal end disposed proximate to the retaining end of the clip, the pusher member being movable axially relative to the tubular member for ejecting the clip distally from the lumen; and
at least one notch located in the distal end of the pusher member for engaging the retaining end of the clip.

3. A method of closing a septal defect within a patient's heart comprising the steps of:
providing a clip having at least two penetrating tines and an opposing retaining end;
advancing the clip, in a biased state, through the patient's vasculature until the clip is disposed within the first chamber of the heart adjacent to the septal opening;
directing the at least two penetrating tines through a flap of tissue to expose the at least two penetrating tines to the second chamber of the heart;
moving the tines of the clip in laterally opposing directions so as to bring the flap of tissue into engagement with the septum wall to at least partially close the septal opening.

4. The method according to claim 3, wherein the tines of the clip are moved by removing the biasing force so as to permit the clip to transition to a relaxed state.

5. The method according to claim 4, wherein the clip is disposed within a distal end of a delivery apparatus comprising a catheter and a pusher member slidably coupled to one another, and wherein the step of advancing the clip comprises advancing the distal end of the delivery apparatus into the first chamber until the distal end is disposed adjacent to the septal defect.

6. The method of claim 5, wherein the step of directing the first end of the clip through the flap of tissue comprises advancing the pusher member distally relative to the catheter, thereby ejecting the clip from within the delivery apparatus.

7. The method of claim 6, wherein the biasing force is removed by ejecting the clip from the delivery apparatus.

8. The method of claim 3, further comprising the step of imaging a portion of the heart.

* * * * *